United States Patent
Sun et al.

(10) Patent No.: US 9,632,055 B2
(45) Date of Patent: Apr. 25, 2017

(54) AUTO-CODED ANALYTE SENSORS AND APPARATUS, SYSTEMS, AND METHODS FOR DETECTING SAME

(75) Inventors: Hoi-Cheong Steve Sun, Tampa, FL (US); Paul M. Ripley, Nanuet, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 523 days.

(21) Appl. No.: 13/881,038

(22) PCT Filed: Nov. 7, 2011

(86) PCT No.: PCT/US2011/059575
§ 371 (c)(1),
(2), (4) Date: Jul. 8, 2013

(87) PCT Pub. No.: WO2012/064648
PCT Pub. Date: May 18, 2012

(65) Prior Publication Data
US 2013/0291626 A1 Nov. 7, 2013

Related U.S. Application Data

(60) Provisional application No. 61/413,374, filed on Nov. 12, 2010.

(51) Int. Cl.
*G01N 27/00* (2006.01)
*G01N 27/327* (2006.01)
*A61B 5/145* (2006.01)

(52) U.S. Cl.
CPC ........... *G01N 27/327* (2013.01); *A61B 5/145* (2013.01); *G01N 27/3272* (2013.01); *Y10T 29/49107* (2015.01)

(58) Field of Classification Search
CPC .................................................... G01N 27/327
(Continued)

(56) References Cited

U.S. PATENT DOCUMENTS 4,473,895 A * 9/1984 Tatematsu ...................... 365/200
5,182,707 A    1/1993 Cooper et al.
(Continued)

FOREIGN PATENT DOCUMENTS

WO   WO 2005/072601    8/2005
WO   WO 2006/103083    10/2006
(Continued)

OTHER PUBLICATIONS

International Preliminary Report on Patentability and Written Opinion of related International Application No. PCT/US2011/059575 mailed May 23, 2013.
(Continued)

*Primary Examiner* — Michael A Lyons
*Assistant Examiner* — Alexander Mercado
(74) *Attorney, Agent, or Firm* — Dugan & Dugan, PC

(57) ABSTRACT

In some aspects, an analyte sensor is provided. The analyte sensor has a plurality of fuse members associated therewith. The fuse members may be burned in sequence and the burn values (related to current, voltage, or time) may be used to extract/decode information. The decoded information may include calibration constant, expiration or manufacture date, counterfeiting codes, warnings, etc. Systems and methods for burning and detecting such burn values of the plurality of fuse members and decoding the coded information related to the sensor are provided, as are numerous other aspects.

25 Claims, 9 Drawing Sheets

(58) Field of Classification Search
USPC .................. 73/61.43; 29/623; 235/435–495
See application file for complete search history.

(56) References Cited

U.S. PATENT DOCUMENTS

| | | | | |
|---|---|---|---|---|
| 5,412,593 | A * | 5/1995 | Magel et al. | 365/96 |
| 5,426,289 | A | 6/1995 | Kinoshita et al. | |
| 5,508,963 | A * | 4/1996 | Sawada et al. | 365/200 |
| 5,572,458 | A * | 11/1996 | Smith et al. | 365/96 |
| 5,645,798 | A | 7/1997 | Schreiber et al. | |
| 5,738,244 | A | 4/1998 | Charlton et al. | |
| 5,759,364 | A | 6/1998 | Charlton et al. | |
| 5,856,195 | A | 1/1999 | Charlton et al. | |
| 6,107,083 | A | 8/2000 | Collins et al. | |
| 6,108,250 | A * | 8/2000 | Kengeri | 365/200 |
| 6,151,238 | A * | 11/2000 | Smit et al. | 365/96 |
| 6,168,957 | B1 | 1/2001 | Matzinger et al. | |
| 6,242,790 | B1 * | 6/2001 | Tsui et al. | 257/529 |
| 6,246,966 | B1 | 6/2001 | Perry | |
| 6,337,507 | B1 * | 1/2002 | Bohr et al. | 257/529 |
| 6,531,040 | B2 | 3/2003 | Musho et al. | |
| 6,590,797 | B1 * | 7/2003 | Nachumovsky et al. | 365/96 |
| 6,841,052 | B2 | 1/2005 | Musho et al. | |
| 6,940,751 | B2 * | 9/2005 | Peng et al. | 365/177 |
| 6,960,287 | B2 | 11/2005 | Charlton | |
| 7,032,823 | B2 | 4/2006 | Nojiri | |
| 7,092,273 | B2 * | 8/2006 | Look | 365/104 |
| 7,118,668 | B1 | 10/2006 | Edelbrock et al. | |
| 7,122,110 | B2 | 10/2006 | Deng et al. | |
| 7,125,481 | B2 | 10/2006 | Musho et al. | |
| 7,330,802 | B2 * | 2/2008 | Hsu | 702/85 |
| 7,402,855 | B2 * | 7/2008 | Kurjanowicz | 257/288 |
| 7,458,002 | B2 * | 11/2008 | Fischer et al. | 714/746 |
| 7,466,416 | B2 | 12/2008 | Baker et al. | |
| 2001/0052646 | A1 * | 12/2001 | Effing et al. | 257/723 |
| 2002/0086319 | A1 | 7/2002 | Ellson et al. | |
| 2003/0110349 | A1 * | 6/2003 | Zimmerman et al. | 711/105 |
| 2004/0179576 | A1 * | 9/2004 | Bowden et al. | 374/163 |
| 2005/0007685 | A1 * | 1/2005 | Winarski et al. | 360/60 |
| 2005/0041051 | A1 | 2/2005 | de Queiroz et al. | |
| 2005/0163657 | A1 * | 7/2005 | Childers et al. | 422/50 |
| 2005/0259123 | A1 * | 11/2005 | Rice et al. | 347/5 |
| 2005/0285761 | A1 | 12/2005 | Jancke | |
| 2006/0039209 | A1 * | 2/2006 | Kawasaki et al. | 365/189.11 |
| 2006/0056246 | A1 * | 3/2006 | Doi | 365/200 |
| 2006/0104475 | A1 | 5/2006 | Jancke | |
| 2006/0189042 | A1 * | 8/2006 | Sakoh et al. | 438/132 |
| 2007/0007621 | A1 * | 1/2007 | Omura et al. | 257/529 |
| 2007/0097745 | A1 * | 5/2007 | Benjamin | 365/185.14 |
| 2008/0055959 | A1 * | 3/2008 | Luich et al. | 365/96 |
| 2008/0101145 | A1 * | 5/2008 | Perry et al. | 365/225.7 |
| 2008/0304347 | A1 * | 12/2008 | Kenkare et al. | 365/225.7 |
| 2009/0001949 | A1 * | 1/2009 | Komori | 323/272 |
| 2009/0068757 | A1 | 3/2009 | Lehmann et al. | |
| 2009/0109725 | A1 * | 4/2009 | Schulte et al. | 365/96 |
| 2009/0166418 | A1 | 7/2009 | Onoda et al. | |
| 2010/0007727 | A1 | 1/2010 | Torre-Bueno | |
| 2010/0017165 | A1 | 1/2010 | Zhong | |
| 2010/0164603 | A1 * | 7/2010 | Hafez et al. | 327/525 |
| 2010/0283120 | A1 * | 11/2010 | Phillips et al. | 257/529 |
| 2010/0288841 | A1 | 11/2010 | Ripley et al. | |
| 2012/0053897 | A1 * | 3/2012 | Naffziger | 702/182 |
| 2012/0179614 | A1 * | 7/2012 | Tang et al. | 705/318 |
| 2012/0179615 | A1 * | 7/2012 | Tang et al. | 705/318 |
| 2013/0298648 | A1 * | 11/2013 | Sun et al. | 73/61.76 |

FOREIGN PATENT DOCUMENTS

| | | |
|---|---|---|
| WO | WO 2007/130280 | 11/2007 |
| WO | WO 2009/061568 | 5/2009 |
| WO | WO 2012/064648 | 5/2012 |

OTHER PUBLICATIONS

International Search Report and Written Opinion of related International Application No. PCT/US2011/059575 mailed Feb. 10, 2012.

* cited by examiner

AUTO-CODED ANALYTE SENSORS AND APPARATUS, SYSTEMS, AND METHODS FOR DETECTING SAME

RELATED APPLICATIONS

The present application claims priority to U.S. Provisional Patent Application No. 61/413,374 filed Nov. 12, 2010, and entitled "AUTO-CODED ANALYTE SENSORS AND APPARATUS, SYSTEMS, AND METHODS FOR DETECTING SAME", which is hereby incorporated herein by reference in its entirety for all purposes.

FIELD OF THE INVENTION

The present invention relates to an analyte sensor including auto-coded information, and apparatus, systems, and methods for reading such auto-coded information.

BACKGROUND

The monitoring of analyte concentration levels in a biofluid (e.g., blood) may be an important part of health management (testing and/or control). For example, analyte sensors (sometimes referred to as "test strips") may be used for the monitoring of a patient's blood analyte level (e.g., glucose levels). In analyte testing, for example, the patient may use a portable lancing device that may be a spring-loaded, trigger-releasable device that receives a single-use, disposable lancet. When the lancet is released, it may prick the user's body part to produce a droplet of blood. That blood droplet may then be transferred to an analyte sensor that may interface with an analyte testing meter, such as a Blood Glucose Meter (BGM), to calculate and display an analyte measurement reading. Based upon the reading, certain control measures may be undertaken by the user.

Accurate analyte detection may therefore be important to ensure desirable control measures are undertaken. The accuracy of such analyte testing meters may be, at least in part, affected by being correctly calibrated. Calibration may be desired to account for batch-to-batch variations in the reagents applied to the analyte sensor. In some instances, calibration information may be manually entered. However, there is a marked trend towards the inclusion of auto-coding on the analyte sensor. In analyte testing meters utilizing auto-coding, the analyte testing meter reads the sensor's calibration information automatically, so that the user need not enter any calibration codes or other information. For example, the auto-coding may, in some existing systems, be accomplished by including multiple electrical contacts in the analyte meter that interface with multiple electrical contacts provided on the analyte sensor. The meter and sensor may then communicate electronically to obtain the auto-coding calibration information.

In multi-strip systems (e.g., ASSENCIA® BREEZE® or BREEZE® 2 Blood Glucose Meters available from Bayer Healthcare, LLC, the auto-coding information may be provided on, and read from, the analyte sensor packaging. This elimination of manual entry of the calibration code information both simplifies the management of the disease for the user, and minimizes any risk of improper manual entry that may affect an accuracy or precision of the analyte detection. However, it may be desirable to allow more simple access to the encoded information, and/or allow more information to be encoded.

It would, therefore, be beneficial to provide analyte sensors, apparatus, systems, and methods that exhibit improved auto-coding capability in terms of simplicity and/or amounts of information that may be encoded.

SUMMARY

In a first aspect, the present invention provides an analyte sensor. The analyte sensor includes a sensor body; first and second electrodes coupled to the body; an active region applied in contact with the electrodes; and two or more fuse members associated with the analyte sensor, the two or more fuse members configured to include coded information concerning the analyte sensor.

According to another aspect, the present invention provides an analyte testing meter adapted to detect auto-coded information concerning the analyte sensor. The analyte testing meter includes first and second electrical contacts adapted to interface with the analyte sensor, the analyte sensor having a plurality of fuse members associated with the analyte sensor, each of the fuse members having a burn value; and a detection circuit adapted to determine the burn values of the plurality of fuse members.

According to another aspect, the present invention provides an analyte testing system, including a port adapted to receive an analyte sensor; an analyte sensor including a plurality of fuse members associated therewith; a detection circuit adapted to produce increasing voltage sufficient to sequentially burn the plurality of fuse members and determine a burn values consisting of a time value, a voltage value, or a current value for each fuse member; and a processor adapted to receive the burn values for each fuse member and decode information associated with the analyte sensor.

According to another aspect, the present invention provides a method of obtaining encoded information. The method includes providing an analyte sensor having a plurality of fuse members associated therewith; and burning the plurality of fuse members to provide decodable information concerning the analyte sensor.

In another method aspect, the present invention provides a method of manufacturing an analyte sensor, including providing a base; forming first and second electrodes on the base; applying an active region in contact with the first and second electrodes; and forming a plurality of fuse members on the analyte sensor, the fuse members containing coding.

In another aspect, the present invention provides an analyte sensor package. The analyte sensor package includes a sealed body containing a plurality of analyte sensors; and a fuse matrix on the sealed body configured to include coded information concerning the analyte sensors.

In another aspect, the present invention provides an analyte sensor including a sensor body; first and second electrodes coupled to the body; an active region applied in contact with the electrodes; and a fuse member associated with the analyte sensor and configured to include coded information concerning a calibration constant of the analyte sensor.

Other features and aspects of the present invention will become more fully apparent from the following detailed description, the appended claims and the accompanying drawings.

DETAILED DESCRIPTION

Figure 1A:
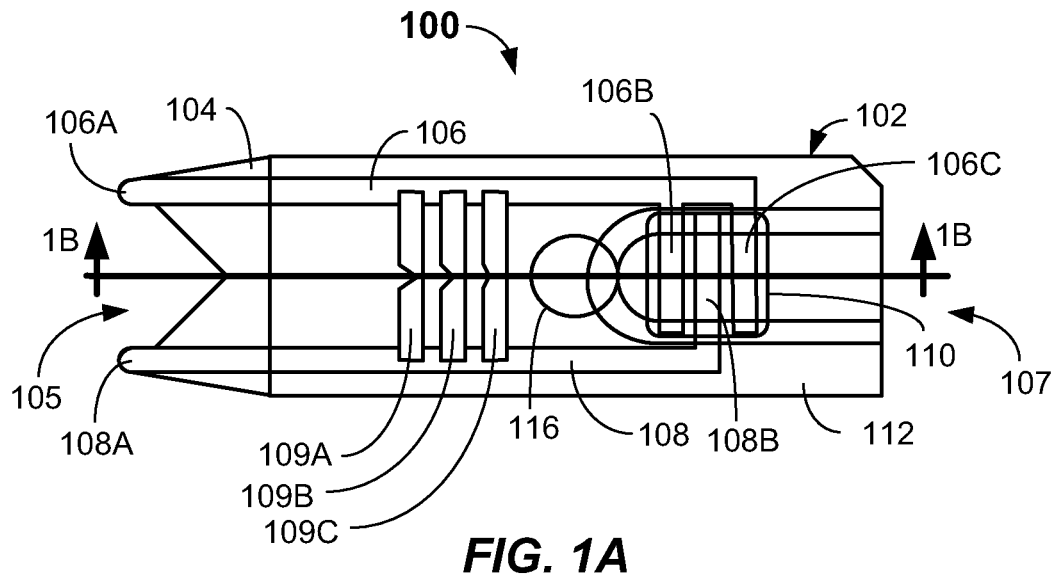
FIG. 1A is a top plan view of an example embodiment of an analyte sensor including a plurality of fuse members provided according to the present invention.

The present invention, according to a first aspect, provides an analyte sensor including associated auto-coded information. The associated auto-coded information is automatically obtained when the analyte sensor or the packaging/cartridge is inserted into and communicates with an analyte testing meter. Therefore, the coded information does not need to be entered by the user. An example analyte sensor according to an aspect of the invention includes a body, and a plurality of fuse members associated with the analyte sensor that are adapted to contain the auto-coded information about the analyte sensor. The auto-coded information may include detailed calibration information (e.g., a calibration constant) about the analyte sensor, and/or other information related to the analyte sensor. In particular, the auto-coded information is contained on a plurality of fuses. Each fuse may be burnt (e.g., blown) by administering a suitable current and/or voltage thereto. The number of fuse members may include two or more, three or more, or four or more, for example. Each of the fuse members may include a different burn value (e.g., a current, applied voltage potential, or time) at which the fuse member will be burnt. A detection circuit of the analyte testing meter is adapted to sequentially burn each of the fuse members and record a burn value there for. These representative burn values may be resolvable into integers adapted to represent coded information. The integers may then used to extract associated auto-coded information. For example, each burn value may be associated with a stored constant or piece of information stored in memory of the analyte testing meter (e.g., in a look-up table).

In some embodiments, the analyte sensor may include a body, first and second electrodes formed on the body, and a plurality of fuse members electrically coupled between the first and second electrodes. Thus, for each sensor including 2 fuse members, many integer pieces of information may be discernable. For example, if the first fuse member has five possible fuse burn options and the second fuse member has five fuse burn options, then 25 separate coded integers may be provided. As should be recognized, using only a small number of fuse members may allow the coding of a vast amount of information. In some embodiments, the fuse members may be included within a fuse matrix to be described more fully herein below. Of course, the finer the burn increments that may be designed and discerned upon burning the fuse member (e.g., every 10 mV), the greater the amount of coded information that may be provided.

In yet another aspect, the present invention provides an analyte testing meter apparatus and system. The apparatus and system includes a detection circuit that is adapted to burn the plurality of fuse members associated with the analyte sensor(s), determine associated burn values, and then decode the auto-coded information associated with an analyte sensor(s). This information concerning the burn values may be processed and decoded to generate a calibration constant, for example, such as by correlating one or more burn values with a look-up table. In some embodiments, the auto-coded information may be adapted to convey other relevant information to a user. Further, the encoded information may be used by the analyte meter solely for internal calculations made thereby.

Auto-coded information that may be provided by the plurality of fuse members may be indicative of at least two pieces of information selected from a group consisting of calibration constant, manufacturing facility, sales territory, expiration date, manufacturing date, prize winner information, inspirational information, instructional information, anti-counterfeiting information, temperature dependent calibration codes, and a unique lot identifying number. The unique lot identifying number may assist the analyte testing meter in recording the number of tests performed from different lots. The unique lot identifying number may be used for uploading along with the analyte sensor testing data to a software package for further analysis. This lot number information may be used by customer support for assisting the diagnosis of user or analyte testing meter errors, and/or by marketing to study the testing habits of customers.

In a further aspect, embodiments of the present invention are directed at methods of providing information to an analyte meter. One method includes providing an analyte sensor including a plurality of fuse members associated therewith, sequentially burning the fuse members, and determining the burn values for each fuse member. Thereafter, the auto-coded information may be deciphered (decoded) and used in calculations carried out by the analyte meter, or used to display or convey other useful and/or relevant information to the user.

These and other embodiments of analyte sensors, analyte testing meters, apparatus and systems for interfacing with the analyte sensors, and methods for using and manufacturing analyte sensors including a plurality of fuse members are described below with reference to FIGS. 1A-11.

Figure 1B:
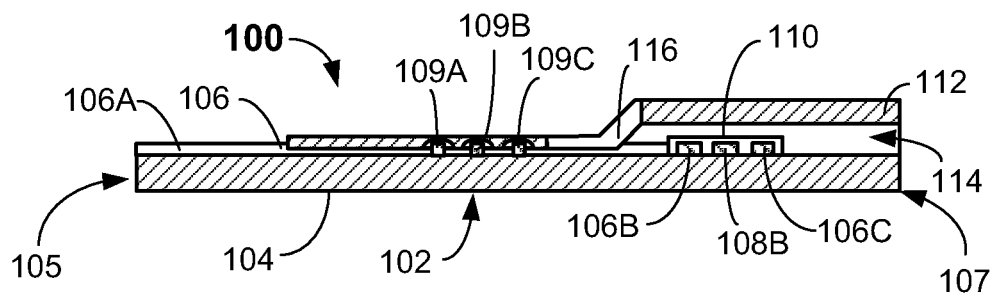
FIG. 1B is a cross-sectional side view of the analyte sensor of FIG. 1A taken along section line "1B-1B."

FIGS. 1A-1B illustrate a first example embodiment of an analyte sensor 100 provided according to a first aspect of the present invention. The analyte sensor 100 may include a body 102 that may include a base 104 onto which the other components of the sensor 100 may be formed or received. The analyte sensor 100 may include a length of between about 15 mm and 35 mm, for example. The analyte sensor 100 may include a maximum width of between about 3 mm and 10 mm, for example. Other length and width dimensions may be used.

The base 104 may be manufactured from any suitable insulating material, such as a polymer material, for example. Suitable polymer materials for the base 104 may include polyvinyl chloride, polycarbonate, polyethylene, dimensionally stable vinyl and acryl polymers, as well as polymer blends such as a polycarbonate and polyethylene therephthalate blend. Other polymer materials may be used. The polymer may include flame retardant materials. In some embodiments, polymers having relatively lower melting points may be used.

In the depicted embodiment, applied to, or otherwise mounted on, the base 104 are a first electrode 106 and a second electrode 108. The electrodes 106, 108 may be applied by a screen printing technique or another suitable technique wherein a pattern of a conductive material is provided on the base 104. For example, in some embodiments, the pattern may be provided by a printing process (screen printing or inkjet printing) wherein a fine trace of conductive material such as an electrode ink (e.g., carbon-based ink) may be applied to form an electrode pattern extending along a longitudinal length of the base 104. Electrode ink including electrochemically-active carbon and silver may also be used.

In some embodiments, a conductive electrode material may be applied (e.g., a noble or other conductive metal) and then laser ablation may be used to create a desired electrode pattern upon a base 104 by ablating/removing some of the material. In some embodiments, the conductive material (e.g., a noble metal such as gold, platinum, palladium, or the like) may be sputter coated onto the base 104 typically through an evaporative process. Other deposition processes may be used. A mask that defines the sensor electrode pattern may be placed in contact with the sputter-coated surface. The mask substrate can be made from quartz with chromium typically being used to define the geometry and pattern of the desired electrodes. Once the mask is in place over the sputter coated surface, a high intensity laser may be directed onto the mask. The conductive material that is exposed to the high energy radiation from the laser is ablated leaving an exposed uncoated base 104. The conductive coating that has been protected by the mask is left unaffected. Thus, the ablation process may define the geometrical configuration of the electrode pattern of electrodes 106, 108.

Figure 7A:
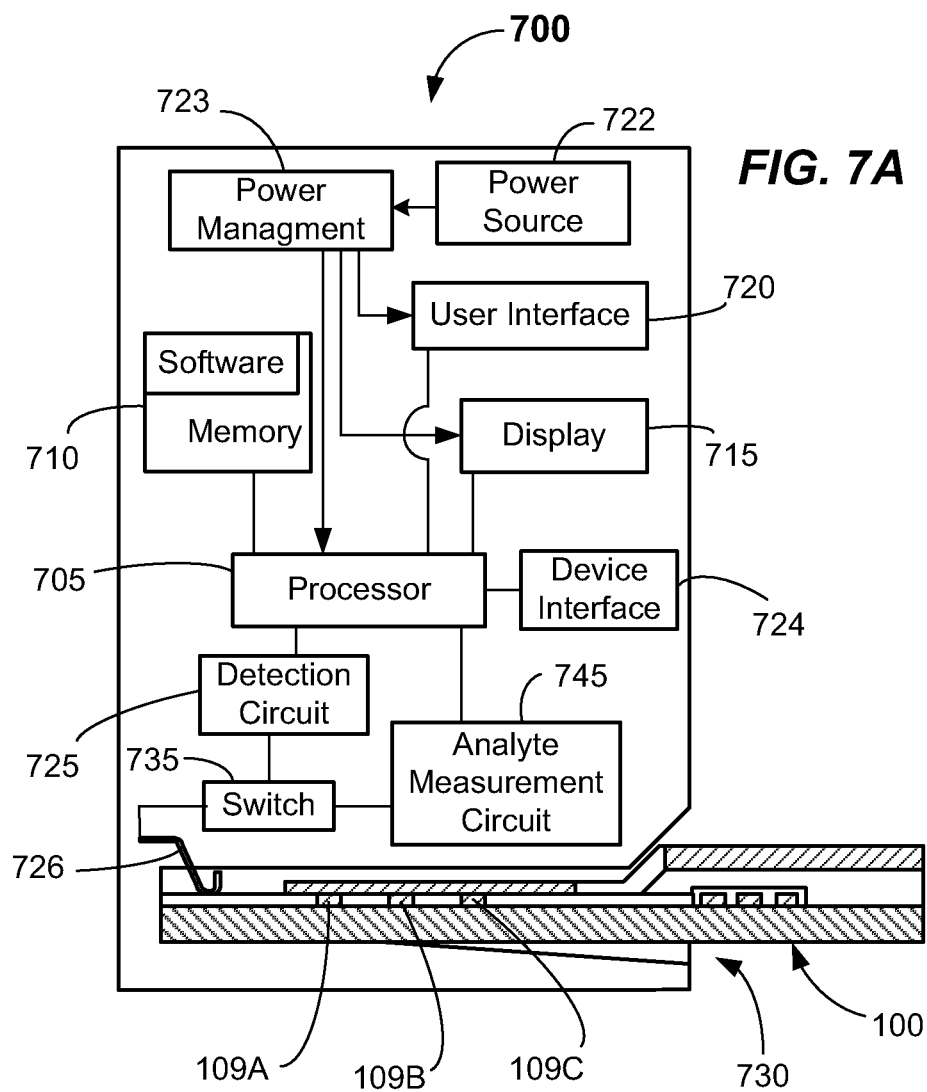
FIG. 7A is a block diagram of an analyte testing meter including detection circuitry according to embodiments of the present invention.
Figure 7B:
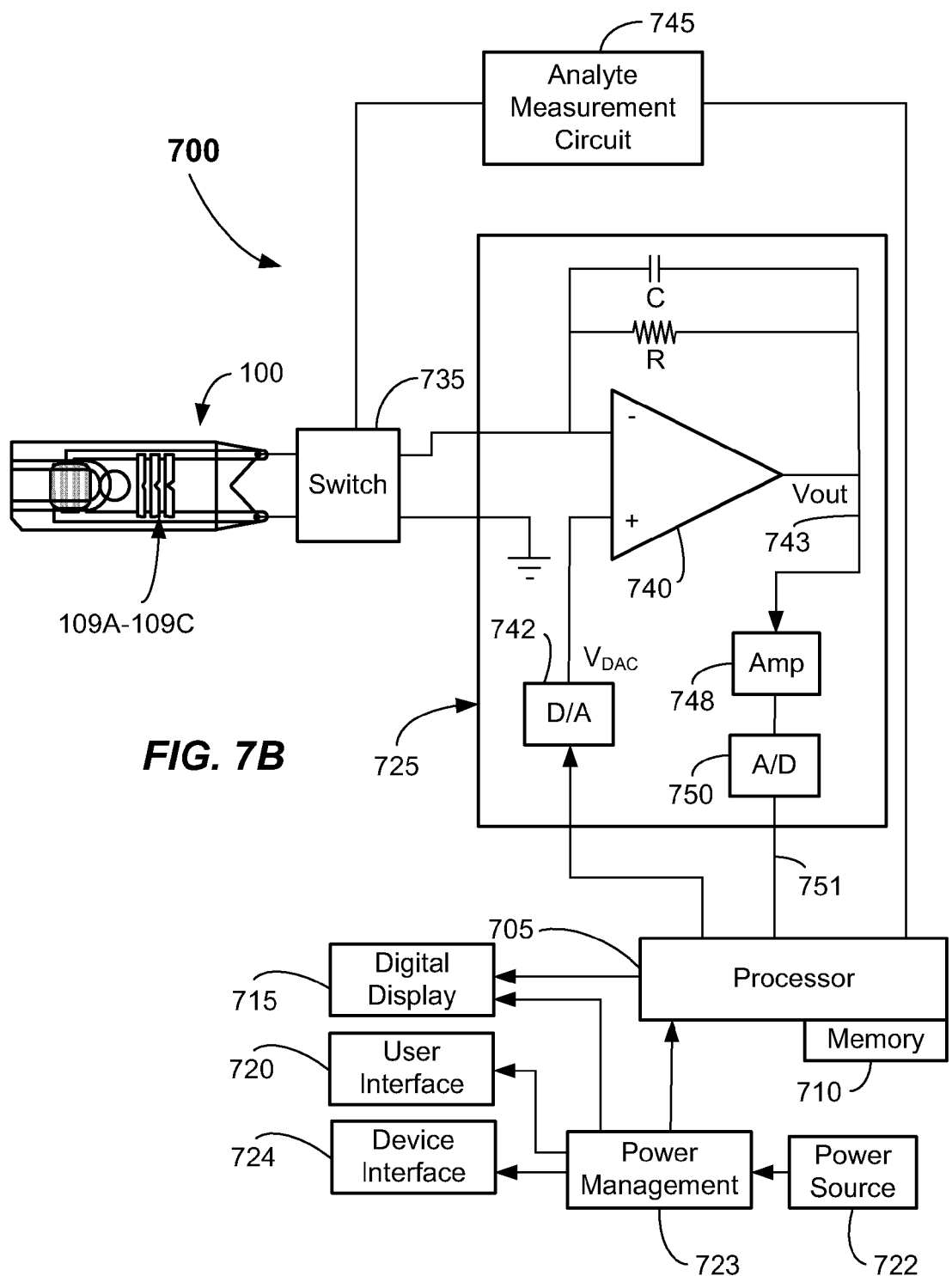
FIG. 7B is a diagram of the analyte testing meter including a detailed detection circuit according to embodiments of the present invention.

The electrodes 106, 108 may include first exposed ends 106A, 108A that are adapted to connect with electrical contacts of an analyte meter (e.g., a suitable analyte meter is depicted in FIG. 7A-7B) so that the analyte sensor 100 may be in electrical communication with the analyte testing meter 700 so as to communicate one or more electrical signals thereto. On the other end of the electrodes 106, 108, the electrode pattern may be provided wherein the electrodes 106, 108 extend in close proximity to each other and may form at least one gap, or even a plurality of gaps, between the electrodes 106, 108.

In the depicted embodiment, the pattern of the first electrode 106 includes first electrode member 106B and a second electrode member 106C formed on a second end of the first electrode 106. The electrode members 106B, 106C may extend across a width of the base 104, for example. The second electrode 108 may include a single electrode member 108B formed on its second end. The single electrode member 108B may be received and interleaved between the first and second electrode members 106B, 106C thereby forming multiple gaps, for example. Other patterns may be used. The electrode patterns 106, 108, as applied, may be about 20 microns or less thick, for example. Other thickness may be used. Furthermore, other thin conductive materials may be used for the electrodes, such as electrically-conductive metal films or strips. Additional patterns for the two electrodes may be found in U.S. Pat. Nos. 6,841,052; 6,531,040; 7,122,110; 7,118,668; and 7,125,481. In some embodiments, additional electrodes may be provided for under fill detection, as is known in the art.

Over a top of the electrode members 106B, 106C and 108B, an active region 110 may be applied. The active region 110 functions to convert an analyte (e.g., glucose, etc.) contained in the bio-fluid sample being analyzed (measured) stoichiometrically into a chemical species measurable in terms of the electrical current generated, or otherwise generate an electrical current that may be generally proportional to an amount of the analyte present in the bio-fluid sample. The electrical current may be conducted by the electrodes 106, 108 and read by a suitable analyte testing meter (See FIG. 7A-7B) in electrical contact therewith. The analyte testing meter 700 may provide a reference voltage (e.g., a voltage bias) during the analyte measurement step. The applied voltage bias may be about 250 mV or less. Other voltage biases may be used depending upon the materials used.

Prior to applying the active region 110, a dielectric layer (not shown) may be provided overtop of the electrodes 106, 108 and base 104 in regions where it is not desired for the active region 110 to be applied. In essence, this dielectric layer application functions as a mask to confine the active region 110 to a precisely defined region (area) proximate to the gaps formed between the electrode members 106B and 108B, and 106C and 108B, respectively. The dielectric layer may include a UV-cured polymer, such as an acrylate modified polyurethane material, and may have a thickness of about 10 microns, for example. Other thicknesses and/or types of insulating materials may be used. The insulating layer may be applied broadly enough so that it covers relatively large areas around the active region 110.

A lid 112 may be provided overtop of the base 104. The lid 112 may be fused or otherwise adhered to the base 104 by application of heat and pressure, or by the application of the above-mentioned UV-cured polymer, for example. Other means of fastening the lid 112 may be employed, such as by the use of an adhesive. The lid 112 may be formed, such as by stamping or heat forming, to have a concave space 114 that may extend from the end 107 towards the location of the active region 110. The concave space 114 may provide a capillary channel into which a bio-fluid may pass. The concave space 114 may have a length of about 2 mm to 5 mm, a width of about 0.5 mm to 1.5 mm, and a height of about 0.05 mm to 0.25 mm, for example. Other dimensions may be used. The lid 112 may be manufactured from a deformable polymer material, such as polycarbonate, an embossable grade of polyethylenetherephthalate, or a glycol modified polyethylenetherephthalate, for example. Other types of materials may be used. The polyurethane dielectric material may be applied over an area encompassed by the lid 112 and may aid in sealing the lid 112 to the base 104. Further details of the structure of the lid 112 and base 104, as well as attachment details may be found in U.S. Pat. No. 5,759,364. A vent 116 in the form of a hole or perforation may be provided at an end of the concave space 114 to improve capillary action and flow of the bio-fluid sample into the concave space 114 from the end 107 when applied thereat by the user.

In accordance with a broad aspect of the invention, the analyte sensor 100 is associated with a plurality of fuse members (e.g., fuse members 109A, 109B, 109C). The fuse members 109A, 109B, 109C may be provided at positions along the length of the electrodes 106, 108. Each of the plurality of fuse members 109A, 109B, and 109C may extend between the first and second electrodes 106, 108. In the depicted embodiment, the fuse members 109A, 109B, 109C may be arranged along the length of the analyte sensor 100 from a first end 105 to the second end 107. Other arrangements may be used. The fuse members 109A, 109B, 109C as shown are provided overtop of the electrodes 106, 108 and in electrical contact therewith. Three fuse members 109A, 109B, 109C are shown, however, it should be understood that any plural number of fuse members may be used, such as two or more, three or more, four or more, etc. Other numbers of the plurality of fuse members may be used. In some embodiments to be described herein, the fuse members are provided as a fuse matrix (see FIGS. 4A-6, FIG. 8, and FIG. 9A-9B). In some embodiments, a single fuse member may be used for encoding a calibration constant. An analyte sensor including a single fuse member extending between the electrodes is disclosed in U.S. Patent Application No. 61/413,365 entitled "TEMPERATURE SENSING ANALYTE SENSORS, SYSTEMS, AND METHODS OF MANUFACTURING AND USING SAME" filed on Nov. 12, 2010, the disclosure of which is hereby incorporated by reference herein in its entirety. This single fuse member may be used to encode a calibration constant for the analyte sensor wherein the calibration constant is related to the burn value of the fuse member. For a particularly well controlled manufacturing process, only a small number of burn value options (e.g., 5-10 possible code options) may be needed for auto-coding of the calibration constant. These codes, as described herein, may be interfaced with a look up table in order to obtain the calibration constant. The burn value of the single fuse member may be based on voltage, current, time, or bit information.

Figure 1C:
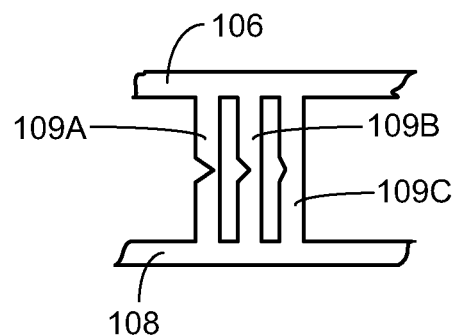
FIG. 1C is a top plan view of another example embodiment of a plurality of fuse members (shown in isolation) provided according to the present invention.

In the depicted embodiment of FIGS. 1A-1C, the fuse members 109A, 109B, 109C are applied to the base 104 of the analyte sensor 100 and respective ends thereof are coupled in electrical contact with the electrodes 106, 108 in an electrical parallel orientation. The larger the number of fuse members that are provided, the larger the amount of auto-coded information that may be provided on the base 104 and associated with the analyte sensor 100.

The auto-coded information may concern or be related to features or properties of the analyte sensor 100 and/or to information that is to be relayed to, or displayed, to the user, or otherwise related to information used by the analyte testing meter (e.g., 700). For example, FIGS. 1A and 1B depict three fuse members 109A, 109B, 109C provided in spaced relationship on the top planar surface of the base 104. In some embodiments, the spaced intervals may be equal (e.g., evenly spaced intervals). Further, the fuse members 109A, 109B, 109C may be centered on a width of the sensor 100, for example. However, optionally, the fuse members 109A, 109B, 109C may be provided on the underside of the lid 112 and electrically connected with the electrodes upon assembly. A detection circuit 725 shown in FIGS. 7A and 7B may determine the burn values for each of the fuse members 109A, 109B, 109C as the analyte sensor 100 is inserted into a port 730 (FIG. 7A) of the analyte testing meter 700.

In the depicted embodiment of FIG. 1A-1B, the fuse members 109A, 109B, 109C may be formed by being printed, marked, or painted, such as by an inkjet, lithography, electrographic printing, or a screen printing. They may be formed in electrical contact with each of the electrodes 106, 108 or electrically connected therewith upon assembly. The fuse members 109A, 109B, 109C may be placed in any suitable position on, or associated with, the body 102, such that they may be burned and burn values for each determined by the analyte meter system 700. In the depicted embodiment of FIGS. 1A and 1B, the fuse members 109A-109C are formed separately from the electrodes 106, 108 and provided in electrical contact therewith through the forming step or assembly step. Optionally, as is shown in FIG. 1C, the fuse members 109A-109C may be formed integrally with the electrodes 106, 108 and may comprise a same material (e.g., a noble metal film such as a gold film) as the electrodes. As shown in FIG. 1A, each of the fuse members 109A, 109B, 109C may be received in a slight pocket or cavity formed between the base 104 and lid 112. The pocket or cavity provides a space for any gases formed during fuse burning to expand into.

Figure 7C:
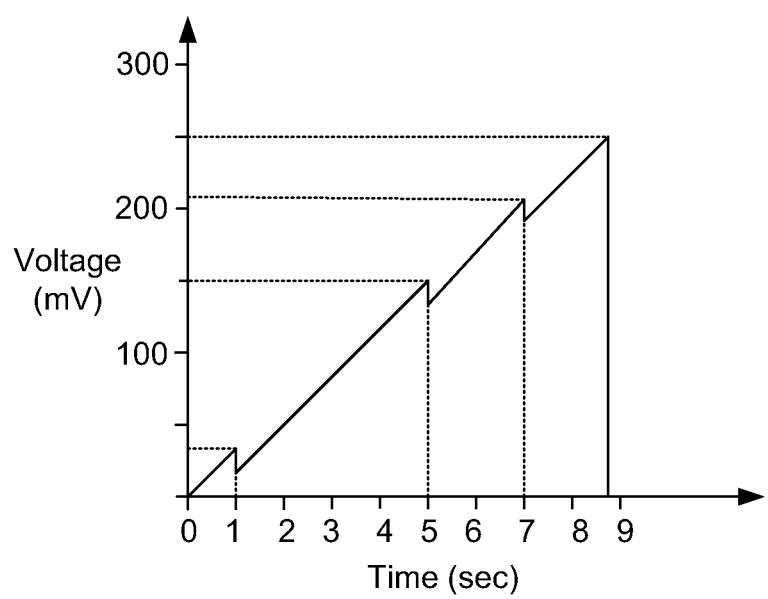
FIG. 7C is a graphical plot of a detected voltage (mV) vs. time (sec) of the detection circuit according to embodiments of the present invention.

Each of the fuse members 109A, 109B, and 109C may include a predefined burn value. The burn value may be a current value, voltage value, or time value at which the fuse will burn (fail). Each fuse burn value for each fuse member 109A, 109B, and 109C may be different. For example, if a voltage is applied, the burn value may be associated with a value of voltage at fuse failure. Fuse failure is defined herein as a condition where the fuse melts sufficiently so that no electrical conduction path is left through the individual fuse member. In other embodiments, the burn value may be related to the maximum current at fuse failure. In yet further embodiments, the burn value may be associated with a time (in seconds) at which the individual fuse member fails, as measured from a start time. The fuse burning step may be accomplished by applying a known input ramp (e.g., a current or voltage ramp as shown in FIG. 7C). The burn value of voltage, current, or time may be stored in memory and used as an input to a routine that uses or correlates that burn value to specific information or data in a lookup table, for example.

Figure 2A:
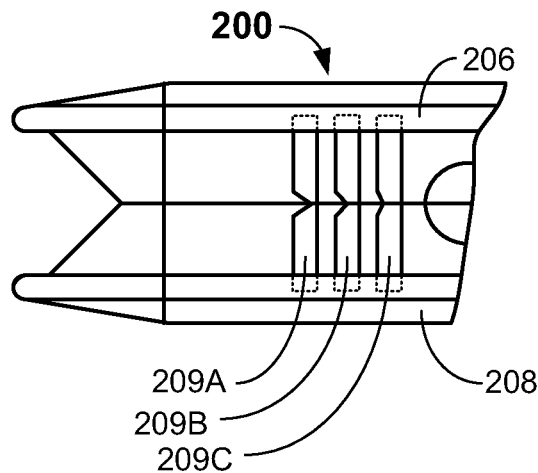
FIG. 2A is a partial top view of another example embodiment of an analyte sensor provided according to the present invention.
Figure 2B:
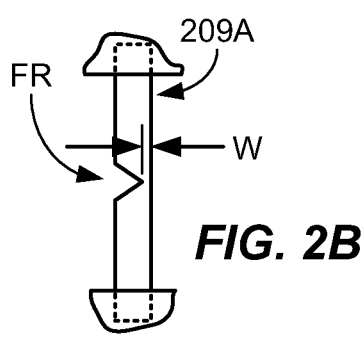
FIG. 2B is a partial top view of a representative fuse member of the embodiment of an analyte sensor of FIG. 2A.

Another embodiment of analyte sensor 200 is described with reference to FIGS. 2A and 2B. This embodiment is similar to the previous embodiment, except that the fuse members 209A, 209B, 209C are provided underneath the electrodes 206, 208. For example, the fuse members 209A, 209B, 209C may be made from a noble metal or other conductive metal and the electrodes 206, 208 may be later applied as a carbon-based material (e.g., a carbon-based fusible ink). As shown in FIG. 2B, each fuse member (e.g., 209A) may include a fuse region FR that is a region of reduced dimension as compared to other parts of the fuse member (e.g., 209A). For example, the fuse region FR may include a notch, groove, or other geometrical feature concentrating resistive heating during fuse burning and causing the fuse member (e.g., 209A) to burn at the fuse region FR. In the FIG. 2A embodiment, each of the fuse members 209A, 209B, 209C have substantially the same fuse body thickness and fuse body width of the body, but the fuse regions FR in each have different notch depths thereby resulting in different fuse region widths W, and thus different burn values for each. Accordingly, the fuse region widths W may be used to design and predefine the burn values for each fuse member and to encode information therein.

Figure 3B:
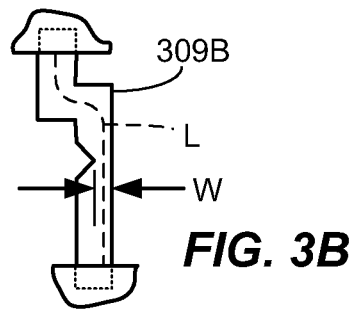
FIG. 3B is a partial top view of a fuse member of the embodiment of an analyte sensor of FIG. 3A.
Figure 3A:
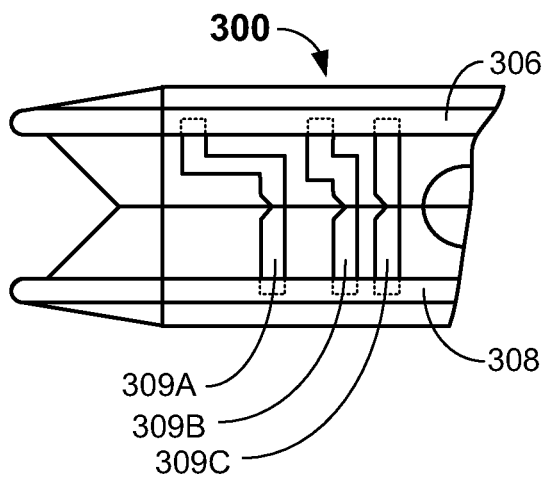
FIG. 3A is a partial top view of another example embodiment of an analyte sensor provided according to the present invention.

Another embodiment of analyte sensor 300 is described with reference to FIGS. 3A and 3B. This embodiment is similar to the previous embodiment, in that the fuse members 309A, 309B, 309C are provided underneath and electrically connected between electrodes 206, 208. Contrarily, each of the fuse members 309A, 309B, 309C have a substantially same fuse region width W (FIG. 3B), but each has a different effective fuse body length L (FIG. 3B). Accordingly, each fuse member 309A, 309B, 309C may have a different designed and predefined burn value that is dependent on the fuse body length L (shown dotted). Longer lengths L at the same notch width W may exhibit relatively higher burn values (e.g., burn voltages).

Figure 4A:
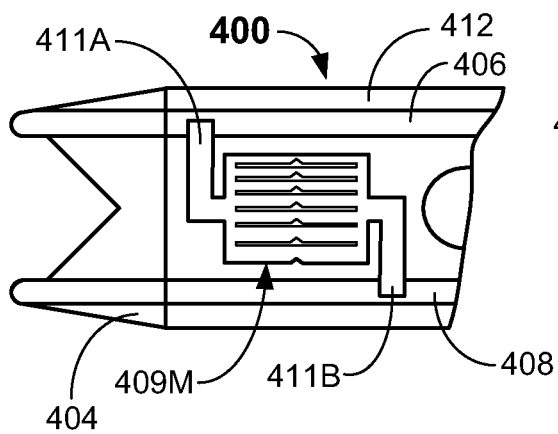
FIG. 4A is a partial top view of another example embodiment of an analyte sensor including a fuse matrix provided according to the present invention.
Figure 4B:
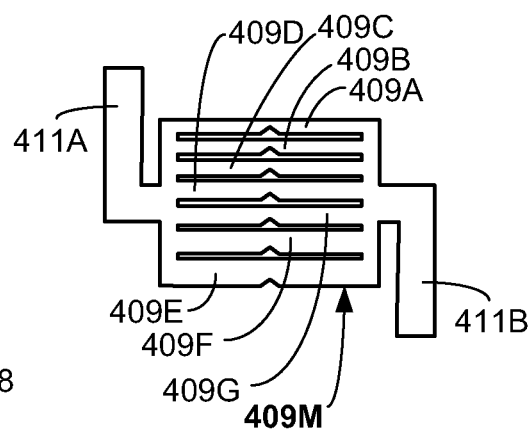
FIG. 4B is an enlarged top view of the fuse matrix utilized in the analyte sensor of FIG. 4A.

Another embodiment of analyte sensor 400 is described with reference to FIGS. 4A and 4B. In this embodiment, the fuse members 409A-409G are provided in the form of a fuse matrix 409M. "Fuse matrix" as used herein means that a plurality of fuse members (e.g., 409A-409G) are included in close proximity to each other and each fuse member shares at least one common connector to an electrode. As shown, two common connectors 411A, 411B electrically connect the fuse matrix 409M to the electrodes 406, 408, respectively. The individual fuse members 409A-409G may each have a different body width and/or fuse region width such that any number of combinations of burn values may be provided. The fuse matrix 409M may include any number of plurality of fuses, such as five or more, ten or more, or fifteen or more, for example. The fuse matrix 409M may be formed as a stand-alone item that may be adhered to the base 404, lid 412, or otherwise deposited (e.g., printed by an carbon-based inkjet process) overtop of, or otherwise in electrical contact with, the electrodes 406, 408.

Figure 5A:
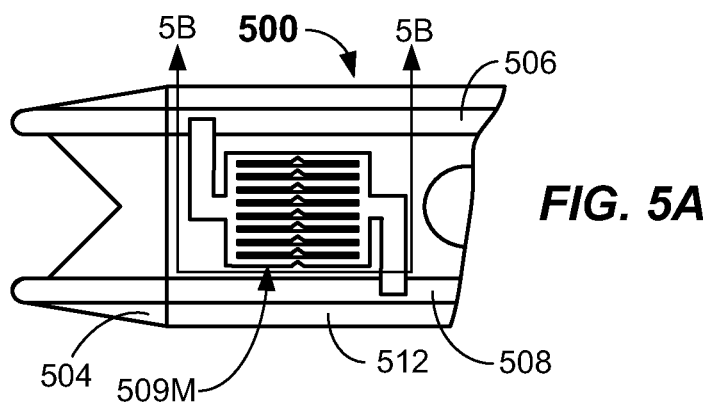
FIG. 5A is a partial top view of another example embodiment of an analyte sensor provided according to the present invention.
Figure 5B:
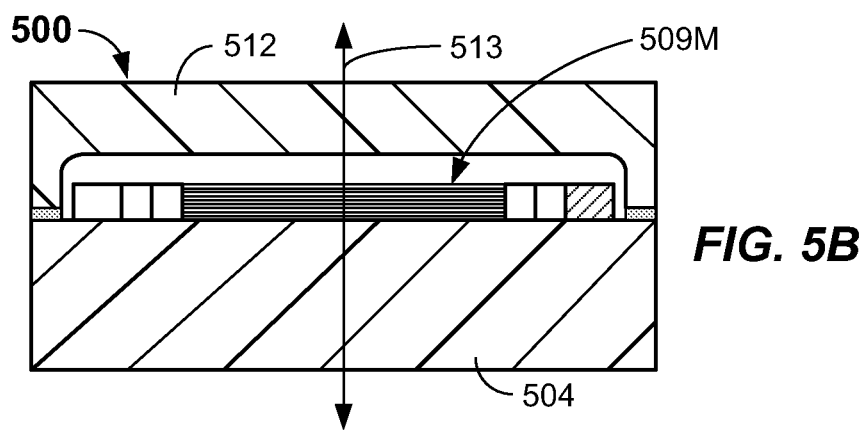
FIG. 5B is a partial cross-sectional side view of the example embodiment of the analyte sensor of FIG. 5A taken along section line "5B-5B."

Another embodiment of analyte sensor 500 is described with reference to FIGS. 5A and 5B. In this embodiment, the fuse matrix 509M is connected to the electrodes 506, 508 as previously described. However, in this embodiment, each of the fuse members of the fuse matrix 509M includes approximately a same body width and fuse region width. A thickness dimension in a normal direction (designated as along axis 513) for one or more fuse members may be different. The thickness may be uniform along most or all of a body length of each fuse member, or may be controlled thickness only on a portion thereof. Thickness of each fuse member of the fuse matrix 409M may be precisely controlled via inkjet printing with a carbon-based fusible ink, for example. Accordingly, a burn value of each fuse member of the fuse matrix 509M may be designed to a predetermined value. Thicknesses of the fuse members of the fuse matrix 509M may be between about 1 microns and about 25 microns. As before, a void or cavity may be provided in the lid 512 in the vicinity of the fuse matrix 509M. A sealant may seal between the lid 512 and base 504 such that no portion of the bio-fluid sample may gain entry into the cavity or make contact with the fuse matrix 509M.

Figure 6:
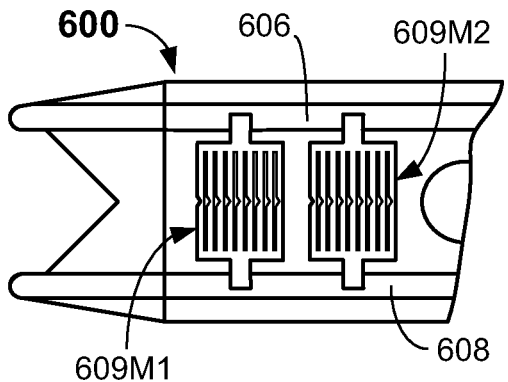
FIG. 6 is a partial top view of another example embodiment of an analyte sensor including multiple fuse matrices provided according to the present invention.

Yet another embodiment of analyte sensor 600 is described herein with reference to FIG. 6. In this embodiment, multiple fuse matrices 609M1, 609M2 are provided in contact with the electrodes 606, 608. The fuse matrices 609M1, 609M2 may be manufactured from any of the constructions previously described.

In more detail, for the three-fuse version shown in FIG. 1A-1B, each of the fuse members 109A, 109B, 109C may have a predetermined burn value that is associated with time (in seconds). Applying a known ramp of voltage at a known ramp rate (e.g., 30 mV/sec) across the electrodes 106, 108 of the analyte sensor 100 will cause each fuse members 109A, 109B, 109C to burn (fail) in a timed sequence. At failure of each fuse member 109A, 109B, 109C, a discontinuity in an output of a detection circuit 725 connected to the electrodes 106, 108 may be measured/sensed (See FIG. 7C). By way of example, in the illustrated embodiment of FIG. 7A-7C, the three burn values are designed to exhibit burn values of 1, 5, and 7 seconds, for the fuse members 109A, 109B, and 109C, respectively. This may provide integers 1, 5, and 7, or a code of 157. These integers or the code may be correlated with a lookup table to decode information concerning the analyte sensor 100. In other embodiments, these burn values (burn time values) may be used directly as inputs to an analyte calculation routine.

In some embodiments, a first time reading associated with a burning of a first fuse member (e.g., fuse member 109A) may correspond to a reference value, and a second time reading may correspond to value that may be correlated to a calibration code to be extracted and utilized by an analyte testing meter as part of an analyte measurement sequence. For example, if the first fuse member fails at a measured value of 33 mV, and it has been determined that the predetermined value should be 1 sec, then the reference may be used to appropriately scale the other burn values so that the other values are more accurately determined.

For example, as shown in Table 1 below, several calibration factors are provided that correspond to burn values of 2-5 for the second fuse 109B. In this manner, a calibration factor may be provided by the burn of a single fuse member (e.g., fuse member 109B).

TABLE 1

Lookup Table - Burn Values vs. Calibration Factors

| | Time (sec) | | | |
|---|---|---|---|---|
| | 2 | 3 | 4 | 5 |
| Calibration Factor | 1.00 | .95 | .90 | 0.85 |

The third fuse 109C may be reserved for values 6-10 that may be used to auto-code additional information concerning the analyte sensor 100. However, if more accuracy of calibration is desired, then two fuse values between 2 and 5 may be used as shown in Table 2.

TABLE 2

Lookup Table - Burn Values vs. Calibration Factors

| Integer | Calibration Factor |
|---|---|
| 12 | 1.05 |
| 13 | 1.04 |
| 14 | 1.03 |
| 15 | 1.02 |
| 23 | 1.01 |

TABLE 2-continued

Lookup Table - Burn Values vs. Calibration Factors

| Integer | Calibration Factor |
|---------|--------------------|
| 24      | 1.00               |
| 25      | 0.99               |
| 34      | 0.98               |
| 35      | 0.97               |
| 45      | 0.96               |

Large amounts of coded information may be provided concerning the analyte sensor 100 with a relatively small number of fuse members.

For example, by using ten fuse members with burn values between 25 mV and 250 mV, ten burn values may be obtained. These ten values may be provided in various combinations and approximately 512 combinations may be obtained. In some embodiments, each fuse member or lack thereof at each respective possible burn value may count for either a 1 bit or 0 bit piece of information, thus with 10 fuse members in a fuse matrix over the possible range of burn vales, for example, many coding possibilities are evident using 1 and 0 bits for the ten different burn values. For example, as shown in Table 3 below, the first burn value (bit 1—illustrating the presence of a burned fuse member) is used as a reference. The second and third possible fuse members are absent at 50 mV and 75 mv, and, thus, a 0 bit may be recorded in memory. As can be seen, many possible coding options are available using either a 0 bit or 1 bit information for each possible fuse member. The better the discrimination (higher number of fuse members) that is achievable below the voltage bias, the higher number of coded pieces of information that may be provided. These encoded bits may be used to interface with a look-up table and extract a stored calibration constant or other information. For example, the first 4 bits may be used for coding a calibration constant, and the other bits may be used for coding other information as discussed herein.

TABLE 3

Lookup Table - Burn Values vs. Bits

| | BURN Value | | | | | | | | |
|---|---|---|---|---|---|---|---|---|---|
| 25 mV | 50 mV | 75 mV | 100 mV | 125 mV | 150 mV | 175 mV | 200 mV | 225 mV | 250 mV |
| Bit 1 | 0 | 0 | 1 | 0 | 1 | 0 | 1 | 0 | 1 |

These burn values may be determined by an appropriate detection circuit. Detection circuit 725 provided in the analyte testing meter 700 is one suitable circuit. Other types of circuits may be used. The burn values may be correlated to information or data in a look-up table, stored in memory, use in calculation(s), or processed and displayed to the user. In some embodiments, a calibration constant may be extracted from one or more of the burn values and used by the analyte testing meter to affect a proper calibration of the analyte measurement calculation for that particular reagent used in that analyte sensor.

In order that the burn values may be easily detectable, it may be desirable to use only burn values that are separated by a predetermined amount. In other words, the burn values should be provided that may be appropriately spaced apart from one another by a sufficient margin. For example, since the range of voltage used to burn the fuse members should be less than the voltage bias used during the analyte measurement step, the number of fuse members that may be used is roughly based upon the discrimination over time, i.e., the number of readings that may be burned between 0 and 250 mV. If the burn value of the fuse member may be very precisely defined and the detection circuit is suitably capable, then as many as 25 fuse members may be used.

In practical application, when an analyte sensor 100 is manufactured, normal manufacturing variations result in differences in the properties of the analyte sensors 100 between lots, and even between batches within lots. Thus, for each batch and/or lot of the analyte sensors produced, there may be a separate calibration constant that may be determined and assigned that will allow an analyte testing meter (e.g., a blood glucose meter) to adjust its internal analyte value calculation by a calibration constant so that an accurate analyte reading is achieved and conveyed to the user. Such calibration constants may be generated for each batch and/or lot. Once a representative number of the analyte sensors have been manufactured and tested, a calibration constant may be assigned for that lot or batch. Once determined, the appropriate fuse members may be associated with the analyte sensors in the lot or batch. In some embodiments, after forming the electrodes 106, 108 on the base, a number of fuse members 109A, 109B, 109C carrying the coded calibration information may be provided overtop and extend between the electrodes as shown in FIG. 1A. Such association may be by printing or otherwise affixing the fuse members or a fuse matrix on the body 102 of the analyte sensor 100. In other embodiments, the fuse members or a fuse matrix may be associated with the analyte sensor by being provided on the packaging for the sensors (e.g., for analyte sensor packages including multiple analyte sensors—See FIG. 9A). This coded information may later be extracted and decoded by an analyte testing meter to determine a calibration constant to be applied in the analyte measurement calculation carried out by the analyte meter and/or otherwise used to convey other information to the user or the analyte testing meter.

Although embodiments of electrochemical analyte sensors have been described herein as one implementation, it should be recognized that the plurality of fuse members or use of a fuse matrix may be applied to any type of analyte sensor, such as a photochromic analyte sensor whereby a change of color of a photochromic material onto which the bio-fluid is applied is measured to detect an analyte concentration level. Likewise, although one application for the analyte sensor of the present invention is for glucose detection, the present invention may be used for analyte sensors for measuring other analytes, such as lactate, keytones, total cholesterol, uric acid, lipids, triglycerides, high density lipoprotein (HDL), low density lipoprotein (LDL), Hemoglobin A1c, etc.

In some embodiments, the plurality of fuse members may be used to designate a date of manufacture, or a date of expiration of a particular batch or lot of analyte sensors 100.

For example the use of certain codes may equate to a particular week of the month. For example, in Table 4 below, various options for week of the month are provided.

TABLE 4

Lookup Table - Burn Values vs. Manufacture Week

| Integer | Week |
|---------|------|
| 67 | 1st |
| 68 | 2nd |
| 69 | 3rd |
| 78 | 4th |
| 79 | 5th |

Another set of codes may equate to a particular month of the year (e.g., to a particular year over a period of years), for example.

Additional codes may be used to code additional information such as manufacturing location, or sales territories into which the analyte sensors 100 are intended to be sold. In some embodiments, a code may also be used for coding a so-called "golden strip," which if received by the user, may reward the user with a prize. For example, if the coded information of the fuse members were to equal a predetermined number stored in memory or in a look-up table upon insertion in an analyte meter, then the user may be rewarded with a free package of sensors or another prize (such as a diabetes supply organizer).

Furthermore, an anti-counterfeiting code may be included in one or more of the codes. For example, certain fuse burn values may be used for a certain manufacturing facility but only for certain months of the year. This code could be preprogrammed into the analyte testing meter, and if the analyte sensor read by the analyte meter did not include the proper code, the analyte meter would designate a warning or error (displaying "counterfeit strip") and may instruct the user to return the strip to the manufacturer of the analyte testing meter for a free replacement, for example. The analyte testing meter may still allow a reading to be displayed, but still display a warning that the reading may be suspect. In this way, the manufacturer of the analyte sensor 100 may be readily placed on notice of potential counterfeiting activity such that corrective measures may be promptly undertaken.

Furthermore, the fuse members may be used to code the correct units of measure (e.g., molarity as expressed by mM/dL, or mass concentration as expressed by mg/dL, or English or metric units) to be used by the analyte testing meter.

In some embodiments, inspirational messages may be equated to a particular code and be displayed on a display of an analyte testing meter. For example, a saying such as "you are taking good care of yourself" or "keep up the good work" may be displayed. Further yet, instructional information may be provided by the codes and displayed or otherwise conveyed to the user when a particular code is detected by the analyte testing meter. All of this useful information may be communicated between the analyte sensor and the analyte testing meter with only a relatively small number of fuse members, such as two or more, three or more, or four or more, five or more, etc.

In accordance with another aspect of the invention, as best shown in FIGS. 7A and 7B, an analyte testing meter 700 is provided. The analyte testing meter 700 includes conventional components, such as processor 705, memory 710, display 715 (e.g., a liquid-crystal display or the like), user interface 720 (e.g., push buttons, keys, a scroll wheel or ball, touch screens, or any combination thereof), power source 722 (e.g., a 3.0 V power source), power management 723, device interface 724, and electrical contacts 726. The processor 705 may be any suitable processor. For example, the processor 705 may be any device or collection of devices that are capable of receiving the signals and executing any number of programmed instructions, and may be a microcontroller, microprocessor, digital signal processor, or the like. For example, a suitable processor is a Cortex M3 equipped microprocessor available from ST Microelectronics or Energy Micro. Data received and/or processed by the processor 705 may be stored in memory 710, which may include software routines that may be adapted to process the analyte data and determine analyte measurement values, and carryout a fuse burning sequence.

In operation, as an analyte sensor 100 including a plurality of fuse members 109A-109C is inserted into a port 730 of the analyte testing meter 700 and contact is made between the electrodes 106, 108 and the electrical contacts 726 (one contacting each electrode 106, 108), the microprocessor 705 (e.g., a System On Chip (SOC)) may be awakened. This may be provided by a resistance measuring circuit in the Analyte measurement circuit 745, for example. A routine in software then causes a switch 735 to engage the detection circuit 725 to enable execution of a checking and/or fuse burning sequence. The switch 735 may be any suitable switch, such as a multiplexor.

The detection circuit 725, as best shown in FIG. 7B, functions to provide a changing voltage across the electrodes 106, 108 of the analyte sensor 100. In particular, the changing voltage may be caused by a ramped voltage input ($V_{DAC}$) being provided to an amplifier 740. A digital signal from the processor 705 may be converted in D/A converter 742 to provide the ramped voltage input. As each fuse member 109A-109C is burnt in sequence due to the preferably linearly increasing voltage applied across the electrodes 106, 108. A tap 743 of the detection circuit 725 may measure a voltage output (Vout). The Vout signal may include a perturbation or discontinuity that is produced by the burning (failure) of each fuse member 109A, 109B, 109C, each of which is detectable.

For example, as shown in FIG. 7C, the first fuse member 109A may burn/fail at time equal to one second, and fuse 109B may burn/fail at a higher voltage potential at five seconds, for example. The third fuse member 109C may burn/fail at yet a higher voltage value at time equals 7 seconds. The Vout signal of tap 743 may be further conditioned via optional amplifier 748 (if needed), and A/D converter 750. An output signal in line 751 may be provided to the processor 705 in digital format, for example. The time burn values of 1, 5, 7 may be used to decode information, by correlating the time burn values with information stored in a lookup table stored in memory 710, for example. Optionally, the raw voltage values may be used to measure the burn values. Such voltage values (burn values) may be correlated with stored information to decode the values. Optionally, measured current or time may be used as the burn values by including a current sensor in the circuit 725.

To determine the burn values, a software routine may execute a slope checking algorithm that may examine the slope of the representative Vout signal in line 751. Following initialization, when a slope is detected that is above a preset threshold value, a time value may be recorded. Each time value represents an encoded piece of information. That time value may be related to the burn value of the respective fuse being burned at that instant. Optionally, voltage or current at fuse burn may be used. These respective burn values may be stored in memory, correlated with a look-up table, and use to extract coded information concerning the analyte sensor 100.

As discussed previously, the first fuse member 109A may be designed to have a burn value of one second. A simple error checking routine may inspect the detected signal Vout in line 751, and if no perturbation is sensed by a preset threshold time (e.g., 1.5 seconds), then the routine may indicate an error. The analyte meter 700 may then output an error code, warning, or message to the user via display 715 indicating that the sensor 100 is used (fuse already burned) or that the sensor is otherwise "defective."

As shown in FIG. 7C, the Vout ramp may continue to a preset voltage value (e.g., at 250 mV) and then return to zero. At this time, switch 735 may be thrown, a suitable voltage bias may be provided across the electrodes 106, 108 that is above the maximum burn value (e.g., about 300 mV), and then the analyte measurement circuit 745 may obtain a raw analyte measurement value. That raw value may be provided to the processor 705. Some of the coded information that was decoded in the previous step may include a calibration constant. That calibration constant may account for batch-to-batch or lot-to-lot variations in the active region 120. This calibration constant may be used by the processor 705 to adjust the raw analyte value to provide a final measured analyte value that may be stored in memory 710, displayed to the user on display 715, and/or transferred to another system (e.g., a desktop or laptop personal computer (PCs), hand-held or pocket personal computer (HPC), compatible personal digital assistant (PDA), and smart cellular phones) or conveyed to a third party via device interface 724.

The processor 705 may centrally manage communications with the other system components, such as the display 715, user interface 724, power management 723, and device interface 724. The processor 705 may also execute instructions and sequences in software routines that may handle the processing of the raw data from the analyte sensor 100 as well as processing and decoding information received from the detection circuit 725.

The device interface 724 may be any suitable Input/Output (I/O) device for allowing data communication with the processor 705 of the analyte testing meter 700, such as wired and/or wireless communications. Wired communications include, for example, communications by universal serial bus (USB) connection. Wireless communications include, for example, radio-frequency (RF) links (e.g., a short-range RF telemetry), infrared (IR) links, and/or Wi-Fi. Some known RF technologies, for example, include Bluetooth® wireless technologies, Zigbee, Z-Sense™ technology, FitLinxx BodyLAN™ system. It should be understood that other communication interface technologies, or protocols, may be employed.

Figure 8:
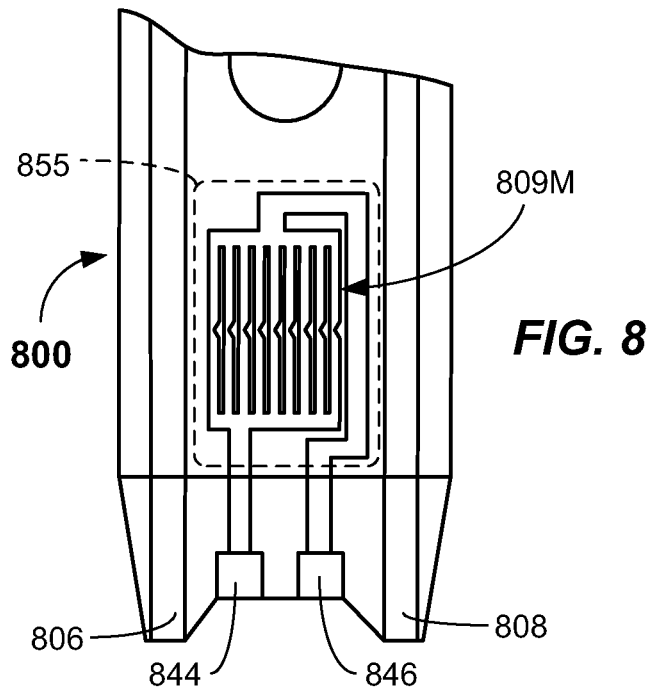
FIG. 8 is a partial top view of another example embodiment of an analyte sensor including a fuse matrix provided according to the present invention.

Additional embodiments of the invention are described with reference to FIG. 8 and FIGS. 9A and 9B. In FIG. 8, a fuse matrix 809M including a plurality of fuse members is associated with the analyte sensor 800. In this embodiment, the plurality of fuse members may be coupled directly to a second set of electrical contacts 844, 846. Again coded information may be provided concerning the analyte sensor 800 by sequentially burning the fuse members and determining burn values for some or all of the fuse members of the fuse matrix 809M. In particular, a decoding circuit like detection circuit 725 may be electrically coupled to the contacts 844, 846 upon insertion of the sensor 800 into an analyte testing meter to carry out extraction of the burn values. A processor may then execute routine to decode information (e.g., calibration constants, etc.) associated with the codes. Electrodes 806, 808 are electrically connected to an active region (not shown, but same as shown in FIG. 1A) and used to obtain the conventional analyte measurement. As discussed before, the matrix 809M may be received adjacent to a sealed cavity 855 (shown dotted) formed in the lid 812, for example. The cavity 855 may function as an expansion zone for gases during fuse burning.

Figure 9A:
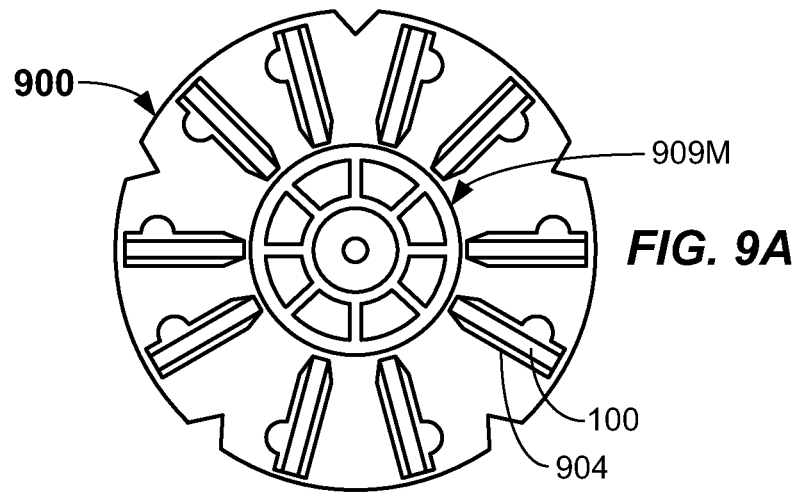
FIG. 9A is a partial top view of an example embodiment of an analyte sensor package including a fuse matrix provided according to another aspect of the present invention.
Figure 9B:
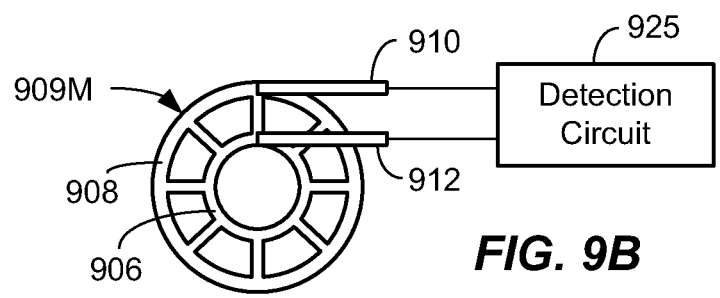
FIG. 9B is a top view of an example embodiment of a fuse matrix of FIG. 9A coupled to a detection circuit according to another aspect of the present invention with the package removed for clarity.

As shown in FIGS. 9A and 9B the use of a plurality of fuse members in a fuse matrix 909M may provide autocoding associated with the analyte sensors 100 (only one labeled) contained in analyte sensor package 900. The package 900 may be a foil package or cartridge that may be received inside of an analyte testing meter (not shown). This sensor package 900 may include a sealed body containing a plurality of identical analyte sensors 100 and a fuse matrix 909M located on the sealed body; the fuse matrix 909M may include a plurality of fuse members configured to include coded information concerning the analyte sensors 100 of the package 900.

The sensors 100 may be received in one or more individual pockets 904 (only one labeled) arranged in the package 900 and the sensors 100 are sealed therein. For example, the pockets 904 may be one or more sealed pockets adapted to seal each sensor 100 around their peripheries. This multi-sensor package 900 is designed in this manner in order to reduce the amount of manual manipulation by the user. The package 900 is installed into the analyte testing meter, and the analyte sensors 100 may be ejected from the package 900 through a port of the analyte testing meter as needed, for example. In the port, the analyte sensor electrodes are coupled to the analyte meter so that the user may apply a droplet of a bio-fluid thereto and carry out analyte measurement testing.

Within each package 900, individual sensors 100 that may be produced from a same manufacturing batch or lot may share the same calibration constant and/or related information (e.g., manufacture date, factory, expiration date, etc.). This calibration code and/or other related information may be placed on the fuse matrix 909M on the actual package 900 that contains the sensors 100 because the calibration code and other related information is common to, and associated with, each analyte sensor 100 in the package 900. The coded information may be encoded on the fuse matrix 909M and the fuse matrix 909M may be positioned on an outside of the package 900 at any suitable location that may be accessed by electrical contacts of a suitable multi-sensor testing meter. The analyte testing meter may include a detection circuit (like circuit 725) for sequentially burning the fuse members of the matrix 909M as previously described herein. Other than the application/addition of a fuse matrix 909M, the package 900 may be made of a foil material, and may be, for example, of the same general construction as described in U.S. Pat. Nos. 5,645,798; 5,738,244; and 5,856,195.

The use matrix 909M may be positioned on either side of the container 900, and may be arranged in any suitable location and/or orientation. For example, as shown in FIG. 9B, the fuse matrix 909M (shown with the body of the package removed for clarity) may be arranged on a front or back surface of a disc-shaped package 900 at a center thereof.

As shown in FIG. 9B, the fuse matrix 909A includes an inner contact ring 906 and an outer contact ring 908. These rings 906, 908 may be contacted by electrical contacts 910, 912 in the analyte testing meter (other components are the same as in FIG. 7A) to couple the fuse matrix 909M to a detection circuit 925. Detection circuit 925 may be the same as described above. Care should be taken in the design of the analyte testing meter to ensure that the package 900 may only be inserted into the meter in an orientation that permits the reading of the fuse matrix 909M.

Figure 10:
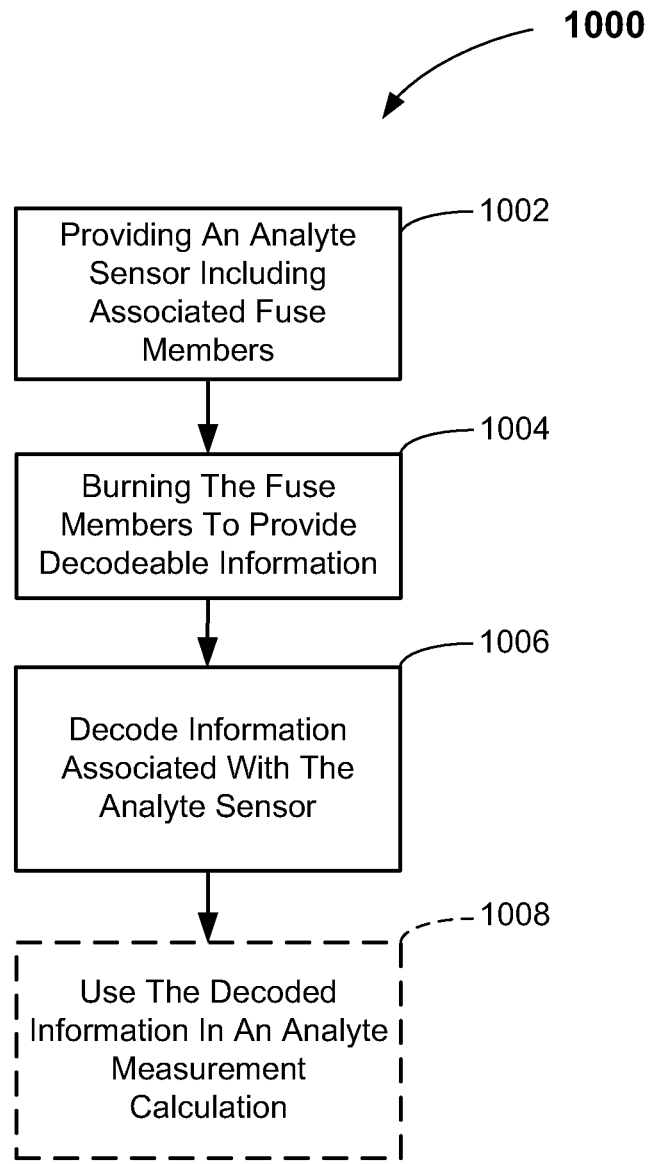
FIG. 10 is a flowchart of a method of using the analyte sensor according to embodiments of the present invention.

As shown in FIG. 10, a method 1000 of providing auto-code information concerning an analyte sensor is provided. The method 1000 may include, but is not limited to, providing an analyte sensor (e.g., 100, 200, 300, 400, 500, 600, 800, 900) having a plurality of fuse members associated therewith in 1002, and burning the plurality of fuse members to provide decodable information concerning the analyte sensor in 1004. The plurality of fuse members may be provided in any suitable form, such as attached between the electrodes as shown in FIGS. 1A, 1C, 2A, 3A, or as a fuse matrix as shown in FIGS. 4A, 5A, 6, 8 and 9A. A detection circuit (e.g., 725, 925) of an analyte testing meter may cause the burning of each of the plurality of fuse members in sequence to provide decodable information concerning the analyte sensor. The decodable information may comprise burn values for each of the fuse members. That information which is associated with the analyte sensor (via being on the sensor itself or on the sensor package) may be decoded in 1006. The decodable information (e.g., burn values) may be correlated with data or information contained in a look up table or otherwise used. Accordingly, a calibration constant and/or other related information may be decoded from the plurality of burn values and used in internal analyte measurement sequence or otherwise used or displayed.

The method 1000 may use at least some of the decoded information in an analyte measurement calculation. For example, the method 1000 may calculate an analyte concentration using an analyte measurement algorithm and use at least some of the decoded information, such as a calibration constant decoded from the encoded information, in the calculation in 1008. Additional decoded information may be used in the calculation, such as information on the proper decoded units of measure, manufacture date, expiration date, etc.

Figure 11:
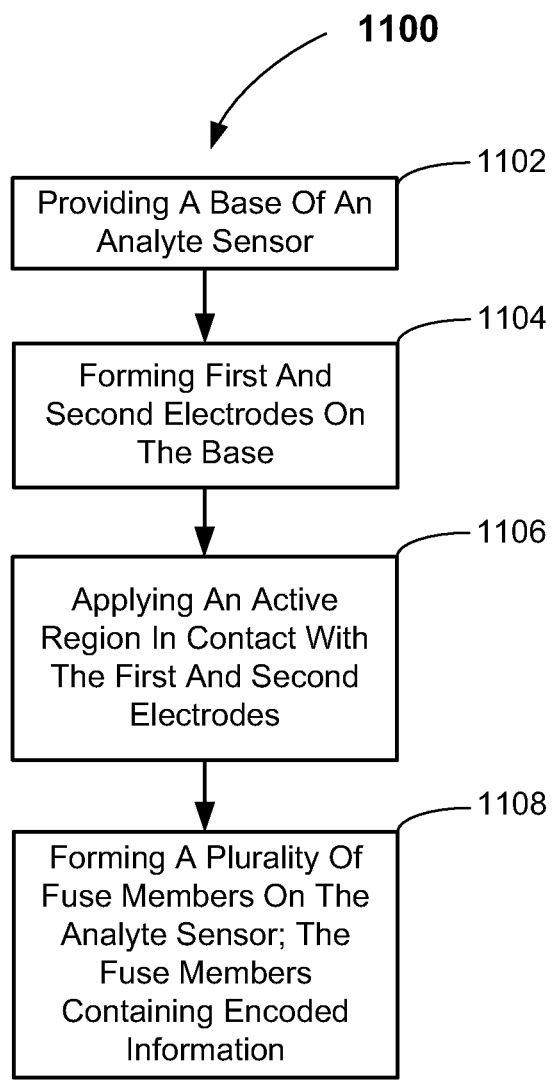
FIG. 11 is a flowchart of a method of manufacturing the analyte sensor according to embodiments of the present invention.

As shown in FIG. 11, a method of manufacturing an analyte sensor is provided. The method 1100 includes providing a base in 1102, forming first and second electrodes on the base in 1104, applying an active region in contact with the first and second electrodes in 1106; and forming a plurality of fuse members on the analyte sensor in 1108, the fuse members containing encoded information.

The foregoing description discloses only example embodiments of the invention. Modifications of the above apparatus, system, and methods, which fall within the scope of the invention, will be readily apparent to those of ordinary skill in the art. Accordingly, while the present invention has been disclosed in connection with example embodiments thereof, it should be understood that other embodiments may fall within the spirit and scope of the invention, as defined by the following claims.

The invention claimed is:

1. An analyte sensor, comprising:
a sensor body;
first and second electrodes coupled to the body;
an active region applied in contact with the electrodes; and
two or more unburned fuse members associated with the analyte sensor, the two or more fuse members configured to include coded information concerning the analyte sensor,
wherein the coded information is encoded in burn values of the unburned fuse members such that the burn values are determined by burning the unburned fuse members.

2. The analyte sensor of claim 1, wherein the two or more fuse members extend between, and are electrically connected to, the first electrode and the second electrode.

3. The analyte sensor of claim 1, wherein the two or more fuse members have different burn values.

4. The analyte sensor of claim 1, wherein the two or more fuse members have burn values having a minimum difference of at least 5% from one another.

5. The analyte sensor of claim 1, wherein the two or more fuse members extend between the first electrode and second electrodes and are formed of a same material as the electrodes.

6. The analyte sensor of claim 1, wherein the two or more fuse members extend between the first and second electrodes and are formed of a different material than the electrodes.

7. The analyte sensor of claim 1 wherein the two or more fuse members extend between the first and second electrodes and the fuse members include fuse bodies with different body lengths.

8. The analyte sensor of claim 1 wherein the two or more fuse members extend between the first and second electrodes and the fuse members include fuse bodies with different body widths.

9. The analyte sensor of claim 1 wherein the two or more fuse members extend between the first and second electrodes and include different width fuse regions.

10. The analyte sensor of claim 1 wherein the two or more fuse members extend between the first and second electrodes and include different thickness fuse regions.

11. The analyte sensor of claim 1 wherein the two or more fuse members are included in a fuse matrix.

12. The analyte sensor of claim 1 wherein the two or more fuse members include burn values that are indicative of at least two selected from a group consisting of calibration information, manufacturing facility, sales territory, expiration date, manufacture date, prize winner information, inspirational information, instructional information, anti-counterfeiting information, temperature dependent calibration codes, and lot identifying number.

13. An analyte testing meter configured to detect auto-coded information concerning an analyte sensor, comprising:
first and second electrical contacts configured to interface with the analyte sensor, the analyte sensor having a plurality of unburned fuse members associated with the analyte sensor, each of the fuse members having a burn value; and
a detection circuit configured to determine the burn values of the plurality of fuse members,
wherein the burn values are determined by burning the unburned fuse members.

14. The analyte testing meter of claim 13, wherein the first and second electrical contacts are adapted to contact a first electrode and a second electrode of the analyte sensor, respectively, wherein the plurality of unburned fuse members is coupled between the first and second electrodes.

15. The analyte testing meter of claim 13, wherein the detection circuit measures a voltage value, current value, or time value for each of the fuse members when each fuse member is burned.

16. The analyte testing meter of claim 13, wherein the detection circuit measures a time value for each of the fuse members when each fuse member is burned.

17. The analyte testing meter of claim 13, wherein the first and second electrical contacts are the only two electrical contacts of the analyte testing meter adapted to electrically contact the analyte sensor.

18. An analyte testing system, comprising:
a port configured to receive an analyte sensor;
an analyte sensor including a plurality of unburned fuse members associated therewith;
a detection circuit configured to produce increasing voltage sufficient to sequentially burn the plurality of fuse members and determine burn values including one of a time value, a voltage value, or a current value for each fuse member; and
a processor configured to receive the burn values for each fuse member and decode information associated with the analyte sensor.

19. A method of obtaining encoded information, comprising:
providing an analyte sensor having a plurality of unburned fuse members associated therewith; and
burning the plurality of fuse members to provide decodable information concerning the analyte sensor,
wherein the decodable information is encoded in burn values of the unburned fuse members such that the burn values are determined by burning the unburned fuse members.

20. A method of manufacturing an analyte sensor, comprising:
providing a base;
forming first and second electrodes on the base;
applying an active region in contact with the first and second electrodes; and
forming a plurality of unburned fuse members on the analyte sensor, the fuse members containing coding, wherein the coding is contained in burn values of the unburned fuse members such that the burn values are determined by burning the unburned fuse members.

21. A method of manufacturing of claim 20, wherein the plurality of fuse members is included in a fuse matrix.

22. A method of manufacturing of claim 20, wherein forming a plurality of unburned fuse members on the analyte sensor comprises forming a fuse body of the fuse members and then machining a fuse region for at least some of the fuse members.

23. An analyte sensor package, comprising:
a sealed body containing a plurality of analyte sensors; and
an unburned fuse matrix on the sealed body configured to include coded information concerning the analyte sensors contained in the analyte sensor package,
wherein the coded information is encoded in burn values of the unburned fuse matrix such that the burn values are determined by burning the unburned fuse matrix.

24. An analyte sensor, comprising:
a sensor body;
first and second electrodes coupled to the body;
an active region applied in contact with the electrodes; and
an unburned fuse member associated with the analyte sensor and configured to include coded information concerning a calibration constant of the analyte sensor,
wherein the coded information is encoded in a burn value of the unburned fuse member such that the burn value is determined by burning the unburned fuse member.

25. The analyte sensor of claim 1 wherein the two or more fuse members extend between the first and second electrodes and the fuse members include fuse bodies with different body thickness.

* * * * *